(12) United States Patent
Chiou et al.

(10) Patent No.: US 7,727,771 B2
(45) Date of Patent: Jun. 1, 2010

(54) SYSTEMS AND METHODS FOR OPTICAL ACTUATION OF MICROFLUIDICS BASED ON OPTO-ELECTROWETTING

(75) Inventors: Pei Yu Chiou, Los Angeles, CA (US); Ming C. Wu, Pacific Palisades, CA (US)

(73) Assignee: The Regents of the University of California, Oakland, CA (US)

( * ) Notice: Subject to any disclaimer, the term of this patent is extended or adjusted under 35 U.S.C. 154(b) by 1316 days.

(21) Appl. No.: 11/209,587

(22) Filed: Aug. 22, 2005

(65) Prior Publication Data

US 2007/0243110 A1 Oct. 18, 2007

Related U.S. Application Data

(62) Division of application No. 10/161,220, filed on May 31, 2002, now Pat. No. 6,958,132.

(51) Int. Cl.
*G01N 1/10* (2006.01)
*G01N 21/01* (2006.01)
(52) U.S. Cl. .................. 436/164; 436/180; 204/603
(58) Field of Classification Search ........... 422/50–104; 204/600–602, 603; 436/180, 164
See application file for complete search history.

(56) References Cited

U.S. PATENT DOCUMENTS

| 4,915,812 | A | 4/1990 | Parce et al. |
| 5,110,727 | A | 5/1992 | Oberhardt |
| 5,156,810 | A | 10/1992 | Ribi |
| 5,500,188 | A | 3/1996 | Hafeman et al. |
| 5,622,872 | A | 4/1997 | Ribi |
| 5,658,723 | A | 8/1997 | Oberhardt |
| 5,919,706 | A | 7/1999 | Tajima |
| 6,197,494 | B1 | 3/2001 | Oberhardt |
| 6,294,063 | B1 * | 9/2001 | Becker et al. ............... 204/450 |

(Continued)

FOREIGN PATENT DOCUMENTS

JP  2000-126606  5/2000

OTHER PUBLICATIONS

Cho et al., "Towards Digital Microfluidic Circuits: Creating, Transporting, Cutting and Merging Liquid Droplets by Electrowetting-Based Actuation", Technical Digest, MEMS 2002, 15th IEEE Conference on Micro Electro Mechanical Systems, Feb. 2002, pp. 32-35.

(Continued)

*Primary Examiner*—Brian R Gordon
(74) *Attorney, Agent, or Firm*—John P. O'Banion (57) ABSTRACT

The invention is related to methods and apparatus that manipulate droplets in a microfluidic environment. Advantageously, embodiments of the invention manipulate droplets by controlling the electro-wetting characteristics of a surface with light, thereby inducing a gradient in the surface tension of a droplet. The gradient in the surface tension propels the droplet by capillary force. A variety of operations, such as transporting, joining, cutting, and creating can be performed. Advantageously, embodiments of the invention obviate the need to create a relatively large and complex control electrode array. A plurality of photoconductive cells or a layer of a photoconductive material selectively couples an electrode carrying an electrical bias to otherwise floating conductive cells in response to a beam of light. The electrical bias applied to the conductive cell generates a localized electric field, which can change the contact angle of the droplet, thereby permitting the droplet to be propelled.

19 Claims, 9 Drawing Sheets

U.S. PATENT DOCUMENTS

| | | | |
|---|---|---|---|
| 6,387,707 B1 | 5/2002 | Seul et al. | |
| 6,445,489 B1 | 9/2002 | Jacobson et al. | |
| 6,565,727 B1 | 5/2003 | Shenderov | |
| 6,766,817 B2 | 7/2004 | da Silva | |
| 6,918,404 B2 | 7/2005 | da Silva | |
| 7,066,586 B2 | 6/2006 | da Silva | |
| 7,312,085 B2* | 12/2007 | Chou et al. | 436/43 |
| 7,329,545 B2* | 2/2008 | Pamula et al. | 436/53 |
| 7,438,859 B2* | 10/2008 | Massaro | 422/100 |
| 7,439,075 B2* | 10/2008 | Fuhr et al. | 436/180 |
| 2001/0001452 A1 | 5/2001 | Moon et al. | |
| 2002/0094580 A1 | 7/2002 | Jorgenson et al. | |
| 2002/0168290 A1 | 11/2002 | Yuzhakov et al. | |
| 2002/0172618 A1 | 11/2002 | Moon et al. | |
| 2003/0006140 A1 | 1/2003 | Vacca et al. | |
| 2003/0011868 A1 | 1/2003 | Zehner et al. | |
| 2003/0012693 A1 | 1/2003 | Otillar et al. | |
| 2003/0224528 A1* | 12/2003 | Chiou et al. | 436/164 |
| 2004/0058450 A1 | 3/2004 | Pamula et al. | |
| 2005/0063875 A1* | 3/2005 | Schatz et al. | 422/100 |
| 2007/0037294 A1* | 2/2007 | Pamula et al. | 436/180 |

OTHER PUBLICATIONS

Ding et al., "Scheduling of Microfluidic Operations for Reconfigurable Two-Dimensional Electrowetting Arrays", IEEE Transactions on Computer-Aided Design on Integrated Circuits and Systems. vol. 20. No. 12. Dec. 2001. pp. 1463-1468.

Hah et al., "A Low Voltage, Large Scan MEMS Micromirror Array with Hidden Vertical Comb-Drive Actuators for WDM Routers", Optical Fiber Communications (OFC) Conferences, 2002 TOPS vol. 20.

Ichimura et al., "Light-Driven Motion of Liquids on a Photoresponsive Surface", Science, Jun. 2, 2002, vol. 88, pp. 1624-1626.

Sun et al., "Photoinduced Surface Wettability Conversion of ZnO and TiO2 Thin Films", J. Phys. Chem. B, 2001, 105, pp. 1984-1990.

Voldman et al., "Holding Forces of Single-Particle Dielectrophoretic Traps", Biophysical Journal, vol. 80, Jan. 2001, pp. 531-541.

Wang et al., "Electrical Molecular Focusing for Laser Induced Fluorescence Based Single DNA Detection", IEEE 15th International Micro Electro Mechanical Systems (MEMS) Conference 2002, pp. 15-18.

http://www.cnde.iastate.edu/ncce/PT_CC/Sec.4.1.1/Sec.4.1.1. html, "Surface Energy (Surface Wetting Capability)", Center for Nondestructive Evaluation, Iowa State University, Ames, IA, pp. 1-4.

* cited by examiner

SYSTEMS AND METHODS FOR OPTICAL ACTUATION OF MICROFLUIDICS BASED ON OPTO-ELECTROWETTING

This application is a divisional of U.S. nonprovisional application Ser. No. 10/161,220 filed on May 31, 2002, now U.S. Pat. No. 6,958,132, incorporated herein by reference in its entirety.

GOVERNMENT RIGHTS

This invention was made with Government support under Contract Number MDA972-00-1-0019 awarded by DARPA. The Government has certain rights in the invention.

BACKGROUND OF THE INVENTION

1. Field of the Invention

The invention generally relates to the manipulation of droplets. In particular, the invention relates to the manipulation or actuation of droplets in a microfluidic circuit.

2. Description of the Related Art

The handling of liquids is fundamental to many fields in science, such as biology and chemistry. To efficiently perform relatively large numbers of tests, miniature laboratory environments have been produced. Conventional miniature laboratories can include relatively intricate, complex, and expensive micro-machined pumps and valves.

One known technique which appears to eliminate the need for micro-machined pumps and valves actuates droplets by electro-wetting. See Cho, S., et al, "Towards Digital Microfluidic Circuits: Creating, Transporting, Cutting and Merging Liquid Droplets by Electrowetting-Based Actuation," *Technical Digest*, 15th IEEE International Conference on Micro Electro Mechanical Systems (2002), pp. 32-35. Disadvantageously, conventional electro-wetting techniques require relatively large and expensive control electrode arrays. In addition, it may be desirable to utilize alternating current (AC) biasing, which can be relatively difficult to switch in an array. As a result, conventional electro-wetting techniques are relatively expensive and can be cost-prohibitive in applications where large amounts of tests are conducted, and the miniature laboratory environments are discarded after a single use. Moreover, the simultaneous control of multiple droplets using conventional electro-wetting techniques may not be achievable as a practical matter due to the impracticality of independently controlling a large number of AC biased electrodes.

One known technique coats a surface with a chemical that reacts with light to change a contact angle and thereby manipulate a droplet. Disadvantageously, such chemical reaction techniques can take on the order of minutes to react and are too slow for practical use. See Ichimura, K., et al., "Light-Driven Motion of Liquids on a Photoresponsive Surface," Science, Vol. 288 (June 2000), pp. 1624-1626. In addition, at least one such technique cannot manipulate water droplets. See Ichimura, K., et al.

Another known technique with zinc oxide (ZnO) or with titanium oxide ($TiO_2$) can change the contact angle of an aqueous or water-based solution. See Sun, et al., "Photoinduced Surface Wettability Conversion of ZnO and TiO2 Thin Films, J. Phys. Chem. B, Vol. 105 (February 2001), pp. 1984-1990. Disadvantageously, ultraviolet light is used to generate the chemical reaction. See Sun, et al. Ultraviolet light can be harmful to biological organisms. Further disadvantageously, the chemical reaction is slow and may require at least 20 minutes to occur. See Sun, et al. Thus, while such chemical reaction techniques may be applicable to "anti-fogging glass and self-cleaning construction materials," see Sun, et al., such chemical techniques may be ill suited to laboratory environments.

What is needed is an efficient and low-cost technique to build an electro-wetting surface.

SUMMARY OF THE INVENTION

Embodiments of the invention advantageously manipulate droplets by controlling the electro-wetting characteristics of a surface with light, thereby inducing a gradient in the surface tension of a droplet. The gradient in the surface tension propels the droplet by capillary force. A variety of operations, such as transporting, joining, cutting, and creating can be performed. Advantageously, embodiments of the invention obviate the need to create a relatively large and complex control electrode array. A plurality of photoconductive cells or a layer of a photoconductive material selectively couples an electrode carrying an electrical bias to otherwise floating conductive cells in response to a beam of light. The electrical bias applied to the conductive cell generates a localized electric field, which can change the contact angle of the droplet, thereby permitting the droplet to be propelled.

One embodiment according to the invention is a microfluidic circuit that is adapted to manipulate a droplet in response to light. It will be understood that a droplet can include a single droplet or multiple droplets. The microfluidic circuit includes a first wall with at least a conductive layer adapted to be coupled to a first terminal of an alternating current (AC) voltage source. The microfluidic circuit further includes a second wall adapted to be coupled to a second terminal of the AC voltage source such that an electric field is generated between the first wall and the second wall, where the second wall is responsive to light such that a portion of the second wall that is illuminated by a localized spot of light has a higher electric field intensity in the insulating layer than a portion of the second wall that is not illuminated by the localized spot of light, wherein at least one of the first wall and the second wall is further adapted to allow light to pass through. A cavity that holds the droplet is defined between the first wall and the second wall.

Another embodiment according to the invention is a microfluidic circuit that is adapted to manipulate a droplet in response to light. The microfluidic circuit includes a first optical electro-wetting structure adapted to be coupled to a first voltage reference, where the first optical electro-wetting structure includes a first insulating layer and at least a first region sensitive to light such that the first region couples the first voltage reference to at least part of the first insulating layer in response to light. The microfluidic circuit further includes a second optical electro-wetting structure spaced apart from the first optical electro-wetting structure, where the second optical electro-wetting structure is adapted to be coupled to a second voltage reference, where the second optical electro-wetting structure includes a second insulating layer and a second region sensitive to light such that the second region couples the second voltage reference to at least part of the second insulating layer in response to light, and where the second optical electro-wetting structure is sufficiently transparent to allow light that impinges on a first area of one side of the second optical electro-wetting structure to pass through and expose a corresponding second area of the first optical electro-wetting structure. A cavity that holds the droplet is defined between the first optical electro-wetting structure and the second optical electro-wetting structure.

Another embodiment according to the invention is a method of manipulating a droplet in a microscale laboratory environment. The method includes providing a first plate and the second plate, holding the droplet between the first plate and the second plate, and selectively illuminating a portion of at least one surface of the first plate and the second plate such that the illuminated portion exhibits a lower contact angle with water than areas that are not illuminated.

Another embodiment according to the invention is a method of manipulating a droplet in a microscale laboratory environment. The method includes providing a first plate and the second plate, holding the droplet between the first plate and the second plate, and selectively illuminating a portion of at least one surface of the first plate and the second plate such that the illuminated portion exhibits a lower contact angle without a light-induced chemical reaction at the surface than areas that are not illuminated.

The illustrated optical electro-wetting techniques permit the fabrication of an all-optical genosensor to be realized. Advantageously, such a genosensor, which detects DNA, can be fabricated without relatively complex mechanical pumps and valves. For example, the optical electro-wetting techniques described herein can be combined with optical techniques to detect DNA. These other techniques can include techniques, such as molecular focusing and detection with dielectrophoretic force and/or electrophoretic force and can further include fluorescence detection, which can be used to detect DNA.

Other embodiments of the invention include a lab-on-a-chip that can advantageously perform advanced laboratory operations, such as separating droplets, without micro-machined pumps and valves.

One embodiment of the invention includes a method of programming an LED array or programming a laser assembly to produce patterns of light that manipulate droplets in an automated fashion.

One embodiment of the invention includes a method of manipulating multiple droplets simultaneously with at least one electro-wetting surface. Another embodiment of the invention includes manipulating a droplet within a space defined between two electro-wetting surfaces, where the opposing surfaces of the two electro-wetting surfaces are activated substantially simultaneously.

BRIEF DESCRIPTION OF THE DRAWINGS

These and other features of the invention will now be described with reference to the drawings summarized below. These drawings (not to scale) and the associated description are provided to illustrate preferred embodiments of the invention and are not intended to limit the scope of the invention.

DETAILED DESCRIPTION OF PREFERRED EMBODIMENTS

Although this invention will be described in terms of certain preferred embodiments, other embodiments that are apparent to those of ordinary skill in the art, including embodiments that do not provide all of the benefits and features set forth herein, are also within the scope of this invention. Accordingly, the scope of the invention is defined only by reference to the appended claims.

Embodiments of the invention advantageously provide the manipulation or actuation of droplets in a microfluidic circuit that can be relatively inexpensively produced. Embodiments of the invention manipulate droplets by controlling the electro-wetting characteristics of a surface with light, thereby inducing a gradient in the surface tension of a droplet. The gradient in the surface tension propels the droplet by capillary force.

Embodiments of the invention thereby permit the manipulation of droplets without relatively intricate and expensive micro-mechanical devices, such as micro-machined pumps and valves. Embodiments of the invention further obviate the need for a large array of control electrodes to control electro-wetting characteristics. See Cho, et al. Rather, embodiments of the invention permit control of the wetting characteristics of a surface by illuminating selected portions of the surface. The illumination can be provided from a variety of sources, such as lasers and arrays of light emitting diodes (LEDs). Advantageously, the elimination of relatively expensive and complicated structures permits embodiments of the invention to be fabricated relatively inexpensively. The reduction in cost promotes the economic feasibility of disposing of lab-on-a-chip units to prevent cross contamination that could occur if such units were reused after an experiment. However, it will also be understood that such units can be reused if so desired. Further advantageously, virtually any polar liquid can be manipulated by the optical electro-wetting surface. Polar liquids include aqueous or water-based solutions, which are frequently encountered in biological environments. Preferably, the aqueous solutions should have a resistivity of not more than $10^7$ $\Omega$-cm.

Figure 1:
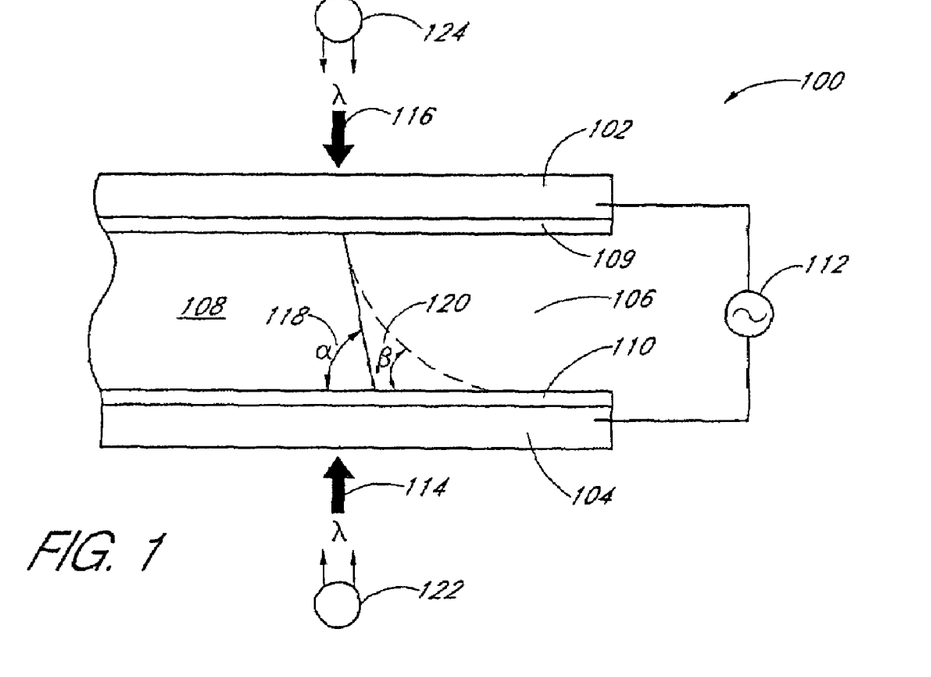
FIG. 1 is a cross-sectional view generally illustrating a microfluidic circuit with one optical electro-wetting surface.

FIG. 1 is a cross-sectional view generally illustrating a microfluidic circuit 100 with one optical electro-wetting surface 110. The microfluidic circuit 100 includes a first wall 102 and a second wall 104. A cavity 106 is defined in the space between the first wall 102 and the second wall 104. The microfluidic circuit 100 accommodates a droplet 108 within the cavity 106.

In the illustrated microfluidic circuit 100, the first wall 102 includes a hydrophobic surface 109 and the second wall 104 includes the optical electro-wetting surface 110. One embodiment of a structure with a hydrophobic surface is described in greater detail later in connection with FIG. 6. Various embodiments of structures with an optical electro-wetting surface are described in greater detail later in connection with FIGS. 3A, 3B, 4A, 4B, 5, and 6.

An electrical bias is applied between the first wall 102 and the second wall 104. In the microfluidic circuit 100 of FIG. 1, an alternating current (AC) voltage source 112 provides the bias. An AC voltage source 112 advantageously permits the manipulation of electrical fields in the presence of insulating layers.

The voltage and frequency characteristics of the AC voltage source 112 can be selected according to materials used in the construction of the microfluidic circuit 100 and according to desired wetting characteristics. In one embodiment, one of the first wall 102 or the second wall 104 is further coupled to ground. The characteristics of the AC voltage source can vary in a broad range. The magnitude of the AC voltage source can vary depending on the thickness and/or dielectric constant of insulation layers. For example, the AC voltage source 112 can supply from about 10 volts (V) to several hundred volts with a frequency from about 10 Hz to about 100 kHz. The AC voltage source 112 can advantageously be configured to supply approximately 100 V at 500 Hz. In one embodiment, the AC voltage source 112 is coupled to the microfluidic circuit 100 with only two conductors or leads. In another embodiment, the AC voltage source 112 is inductively coupled such that no electrical leads are required for the AC voltage source 112 to couple to the microfluidic circuit 100. The AC frequency can be tuned such that the impedance from the photoconductor dominates over that from the insulator in the dark.

Light is applied to a selected portion of the second wall 104 of the microfluidic circuit 100. A light source 122 can be configured to apply light directly to the second wall 104, as illustrated by a first light beam 114. Another light source 124 can alternatively or in addition be configured to apply light indirectly to the second wall 104 via the first wall 102, as illustrated by a second light beam 116. Where the light passes through the first wall 102 to reach the second wall 104, the first wall 102 should be transparent enough to permit the light to pass through and activate the optical electro-wetting characteristic of the desired portion of the second wall 104.

In one embodiment, which will also be described in greater detail later in connection with FIGS. 3A and 3B, the second wall 104 includes an insulating layer and a photoconductive layer that are arranged in series with the voltage bias. A voltage reference, which can be a ground reference, is coupled to the photoconductive layer. The conductivity of the photoconductive layer varies with light. In a "dark" state, i.e., not specifically illuminated by light, the photoconductive layer has a relatively high resistance, and a substantial amount of the voltage between the first wall 102 and the second wall 104 is dropped across the photoconductive layer. In one embodiment, ambient light, such as from room lighting, does not significantly activate the photoconductive layer. As a result, relatively little voltage is dropped across the insulating layer, and there is relatively little electric field generated in and around the insulating layer. As a result, the droplet 108 exhibits a relatively large contact angle, α 118. The contact angle is the angle formed by the solid/liquid interface and the liquid/vapor interface as measured from the side of the liquid.

In an illuminated state, the photoconductive layer has a relatively low resistance and relatively little of the applied voltage drops across the illuminated portion of the photoconductive layer. Rather, the bulk of the voltage is dropped across the insulating layer, which results in relatively large electric fields in the corresponding areas. As a result, the droplet 108 exhibits a smaller contact angle, β 120.

Equation 1 approximately models the contact angle, θ, of the droplet at the interface of the insulating layer as a function of the voltage, $V_A$, dropped across a corresponding region of the insulating layer.

$$\cos[\theta(V_A)] = \cos[\theta(0)] + \frac{1}{2}\frac{\varepsilon}{d\gamma_{LV}}V_A^2 \quad \text{(Eq. 1)}$$

In Equation 1, which is also known as Lippman-Young's equation, θ(0) corresponds to the contact angle without an applied voltage. This approximately corresponds to the situation when a photoconductive layer is in a dark state so that the voltage drop, $V_A$, across the insulating layer is relatively low. The variable $\varepsilon$ corresponds to the permittivity of the insulating layer (product of the dielectric constant, $\varepsilon_r$, and the permittivity of free space, $\varepsilon_0$). The variable d corresponds to the thickness of the insulating layer, i.e., the thickness across which the voltage, $V_A$, is dropped. When the applied voltage is AC, a root mean square (RMS) value for voltage is used in Equation 1. The variable $\gamma_{LV}$ corresponds to the interfacial tension between the liquid forming the droplet to be manipulated and the environment within the cavity 106. Typically, the droplet is in a vapor environment, such as the atmosphere. However, it will be understood that the environment can include another liquid (such as an oil) with a different surface tension than the liquid forming the droplet that is to be manipulated, and the environment can also include vacuum.

To transport or otherwise manipulate the droplet, a gradient in the electric field is generated by the spot of light, and the resulting asymmetry in the contact angles can apply force to the droplet via capillary action. As will be described later in connection with FIGS. 8A-D, the manipulation of a droplet can include transporting the droplet, joining multiple droplets to one, cutting or separating a droplet into at least two smaller droplets, and creating a droplet from a reservoir of fluid.

Figure 2:
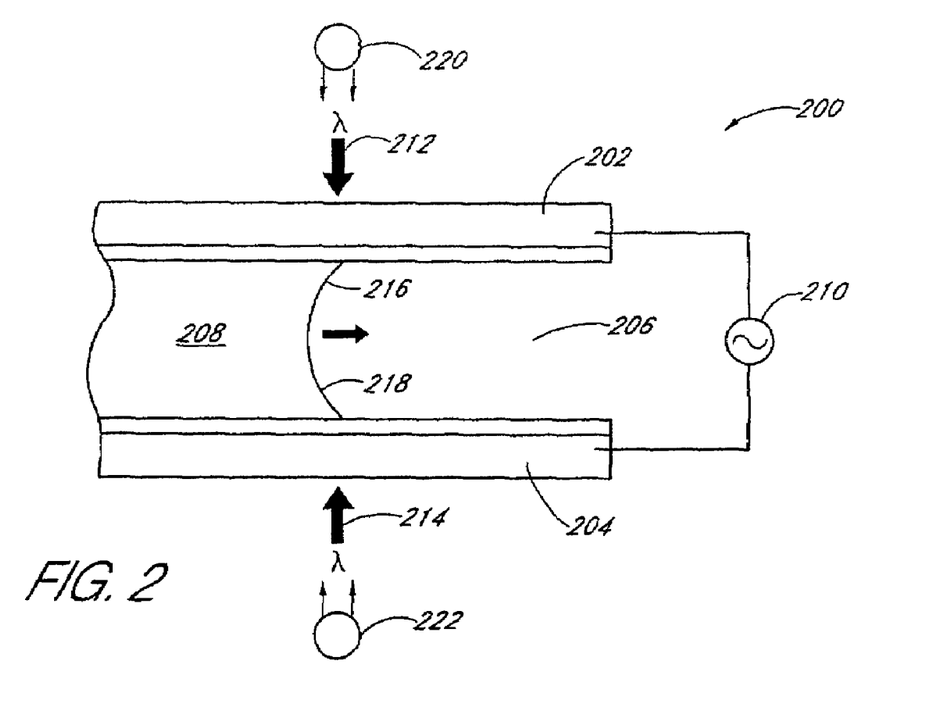
FIG. 2 is a cross-sectional view generally illustrating a microfluidic circuit with two optical electro-wetting surfaces.

FIG. 2 is a cross-sectional view generally illustrating a microfluidic circuit 200 with two optical electro-wetting surfaces. Advantageously, the changing of the contact angles of a droplet with respect to two optical electro-wetting surfaces can provide enhanced capillary force, which can be used to permit the droplet to be transported faster, to be manipulated in more ways, to be manipulated with less bias voltage, and the like.

The microfluidic circuit 200 includes a first optical electro-wetting structure 202 and a second optical electro-wetting structure 204. A space 206 defined between the first optical electro-wetting structure 202 and the second optical electro-wetting structure 204 accommodates a droplet 208.

A voltage bias is applied between the first optical electro-wetting structure 202 and the second optical electro-wetting structure 204. In the illustrated embodiment, an AC bias 210 is used.

Light can be selectively applied to one side or to both sides of the microfluidic circuit 200, as shown by a first light beam 212 from a first light source 220 and a second light beam 214 from a second light source 222. Preferably, at least one of the first optical electro-wetting structure 202 and the second optical electro-wetting structure 204 is sufficiently transparent, such that light that is applied to only one side of a sufficiently transparent optical electro-wetting structure activates the sufficiently transparent optical electro-wetting structure and also passes through and activates a corresponding area of the other optical electro-wetting structure. One embodiment of a relatively transparent optical electro-wetting structure is described in greater detail later in connection with FIG. 5. In one embodiment, the first optical electro-wetting structure 202 and the second optical electro-wetting structure 204 are identical, but it will be understood that different structures for each can be used.

The contact angles of the droplet 208 are thereby manipulated at both optical electro-wetting structure surfaces, as illustrated by a first contact angle 216 and a second contact angle 218.

Figure 3A:
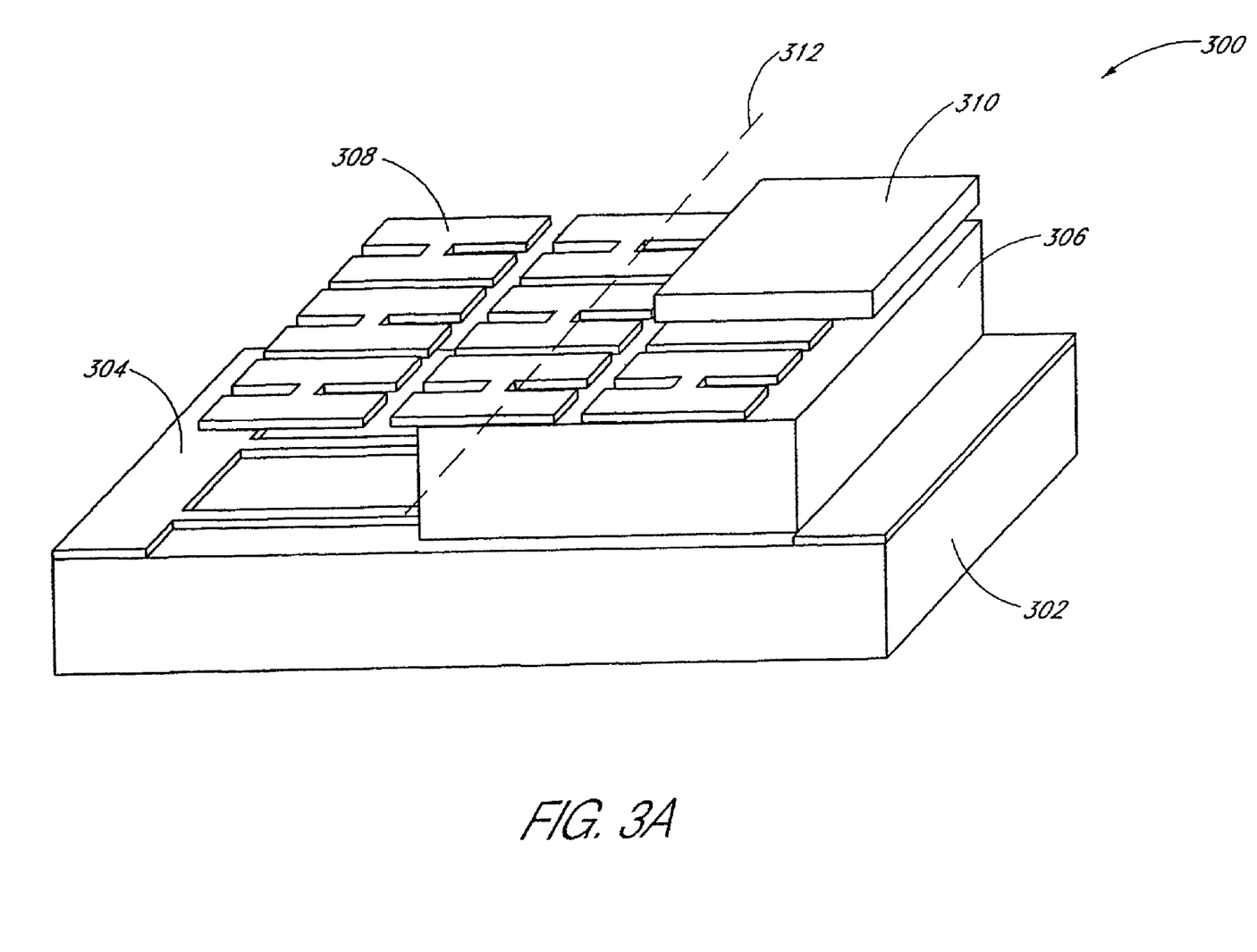
FIG. 3A is a perspective view of one embodiment of a substrate assembly that can provide an optical electro-wetting surface.

FIG. 3A is a perspective view of one embodiment of a substrate assembly 300 that can provide an optical electro-wetting surface. For the purposes of clarity, the perspective view of the substrate assembly 300 in FIG. 3A is illustrated in a cutaway and exploded manner. The illustrated substrate assembly 300 includes a base layer 302, an electrode layer 304, a layer of photoconductive material 306, a plurality of conductive cells 308, and an insulating layer 310. It will be understood that the size of the substrate assembly 300 can vary in a very broad range and that only a relatively small portion of the substrate assembly 300 is shown in FIG. 3A.

The base layer 302 is preferably formed from an insulating material. The base layer 302 can be made from a variety of materials, such as silicon oxide ($SiO_2$), glass, plastic, and others. Where light is applied from the base layer side of the substrate assembly 300, a relatively transparent material should be selected for the base layer 302. However, it will be understood that in some configurations, a microfluidic circuit can be configured so that light can be applied through the opposing surface, rather than through the base layer 302, so that the base layer 302 need not be transparent.

The electrode layer 304 is formed above the base layer 302 as shown in FIG. 3A. It will be understood by one of ordinary skill in the art that the electrode layer 304 can be formed prior to or after the forming of the base layer 302. The electrode layer 304 permits the substrate assembly to be coupled to a voltage reference. It will be understood by one of ordinary skill in the art that the voltage reference can include a ground reference, as well as an AC voltage reference. The electrode layer 304 can be formed as a solid plane, as a gridded plane, as lines of conductors, and the like. In the illustrated embodiment, the electrode layer 304 includes rows of approximately parallel conductors that are electrically connected to the same potential. The amount of current that is carried by the electrode layer 304 is relatively small, and the electrode layer 304 can be fabricated from a wide variety of conductive materials. In one embodiment, the electrode layer 304 is formed from aluminum. Where light is applied from the base layer 302 side of the substrate assembly, a relatively transparent conductor, such as indium tin oxide (ITO), can be used.

The layer of photoconductive material 306 is formed between the electrode layer 304 and the conductive cells 308. The layer of photoconductive material 306 exhibits relatively low conductivity when dark, and relatively high conductivity when illuminated by a light source. Preferably, the layer of photoconductive material 306 is selected to be responsive to visible light, such that proper operation can be efficiently verified. In addition, a relatively short electron-hole pair recombination time can provide advantageously fast switching.

In one embodiment, the selected photoconductive material corresponds to a material with a dark conductivity in the range of about $10^6$ to about $10^{11}$ Ω-cm. One example of a suitable material for the layer of photoconductive material 306 is amorphous silicon, which has a dark conductivity of approximately $10^8$ Ω-cm. In one embodiment, light with a wavelength between about 400 nm and about 1100 nm is used to illuminate portions of amorphous silicon. The light intensity for activating optical electro-wetting can be advantageously low. An exemplary light intensity for switching amorphous silicon is about 65 mW/cm$^2$. The layer of photoconductive material 306 permits optical control of a voltage dropped across a corresponding portion of the insulating layer 310.

The insulating layer 310 is formed above the conductive cells 308. In a microfluidic circuit, the insulating layer 310 is disposed between the chamber that accommodates a droplet and the conductive cells 308. In one embodiment, the insulating layer 310 includes a stack of a relatively thick layer of silicon oxide ($SiO_2$) and a relatively thin layer of polytetrafluoroethylene (PTFE), where silicon oxide is disposed between the relatively thin layer of PTFE and the conductive cells 308. PTFE is also known as Teflon®. In one embodiment, the layer of PTFE is relatively thin compared to the layer of silicon oxide, such that a voltage drop across the layer of silicon oxide is relatively high compared to a voltage drop across the layer of PTFE. Where the light that activates the layer of photoconductive material 306 passes through the insulating layer 310, the insulating layer 310 should be relatively transparent. For example, a layer of PTFE can be formed with a sufficiently thin thickness that permits light to pass through without substantial attenuation.

A beam of light selectively applied to the layer of photoconductive material 306 generates a region of relatively low resistance in the layer of photoconductive material 306. Advantageously, this region of relatively low resistance selectively couples a conductive cell 308 or group of conductive cells 308 to the electrode layer 304 and thus, to the corresponding voltage reference. It will be understood that the photoconductive material does not have to fill the entire layer of photoconductive material 306. For example, the layer of photoconductive material 306 can be formed from a layer of insulating material with vias filled with photoconductive material that are arranged to selectively couple the conductive cells 308 to the electrode layer 304.

The selective coupling through the layer of photoconductive material 306 notwithstanding, the conductive cells 308 are electrically isolated from each other such that the layer of photoconductive material 306 can selectively couple an individual conductive cell 308 or a group of conductive cells 308 to the electrode layer 304. The conductive cells 308 can be made from a variety of conductive materials. In one embodiment, where the light that activates the photoconductive material passes through the insulating layer 310 and the conductive cells 308, the conductive cells 308 can be formed from a relatively transparent material, such as indium tin oxide (ITO).

The coupling of a selected conductive cell to the electrode layer 304 ties the potential of the selected conductive cell to the potential of the electrode layer 304. The corresponding portion of the insulating layer 310 between the selected conductive cell and the droplet thereby has a correspondingly large voltage drop, which gives rise to a relatively large electric field and low contact angle. By contrast, an unselected conductive cell, i.e., a conductive cell corresponding to a dark region of photoconductive material, is not tied to the potential of the electrode layer 304. Rather, the voltage drop from the surface of the insulating layer 310 (on the chamber side) to the electrode layer 304 is divided between the layer of photoconductive material 306 and the insulating layer 310. Preferably, when not activated by light, the voltage drop across the layer of photoconductive material 306 is relatively large compared to the voltage drop across the insulating layer 310. As a result, regions of the insulating layer 310 corresponding to non-illuminated regions of photoconductive material correspondingly have relatively little electric field strength and relatively high contact angles for a droplet. This gradient in contact angle allows the droplet to be manipulated.

This optical activation of electrical coupling advantageously obviates the need to provide an array of individually selectable control electrodes to generate a localized electric field, thereby permitting electro-wetting devices to be economically fabricated at relatively low cost. In the illustrated substrate assembly 300, the photoconductive material selectively couples a conductive cell substantially in a "vertical" direction, i.e., through a layer, in response to light. In other configurations, such as the configurations described later in connection with FIGS. 4A, 4B, and 5, the photoconductive material selectively couples a conductive cell substantially in a "horizontal" direction, i.e., substantially laterally within the layer.

Figure 3B:
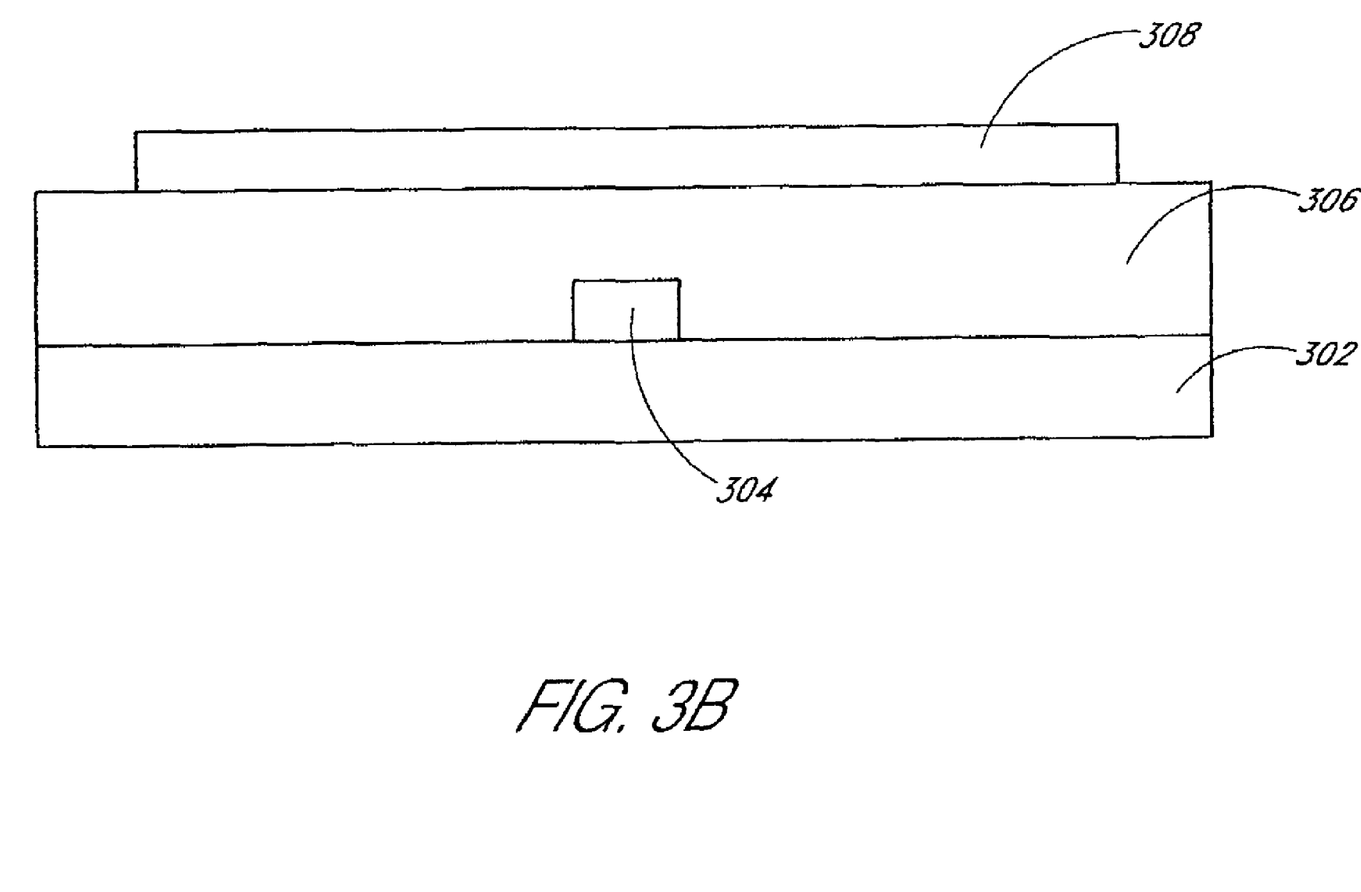
FIG. 3B is a cross-sectional view of a portion of the substrate assembly of FIG. 3A.

FIG. 3B is a cross-sectional view of a portion of the substrate assembly of FIG. 3A. The cross-sectional view is taken along a dashed line 312 of FIG. 3A. The cross-sectional view shows an electrode from the electrode layer 304 on the base layer 302. The layer of photoconductive material 306 is disposed between the conductive cell 308 and the electrode from the electrode layer 304. Without light or with only ambient light, the layer of photoconductive material 306 insulates the conductive cell 308 from the electrode from the electrode layer 304. When the layer of photoconductive material 306 is illuminated, the layer of photoconductive material 306 couples the conductive cell 308 to the electrode with a relatively low resistance.

In the embodiment illustrated in FIGS. 3A and 3B, the conductive cells 308 are approximately centered over conductive lines of the electrode layer 304. Although the conductive cells 308 and the electrode layer 304 can correspond to a variety of shapes and configurations, the illustrated conductive cells 308 are further patterned into "H" shaped patterns, and the electrode layer 304 can include relatively long lines to reduce parasitic capacitance between the conductive cells 308 and the electrode layer 304. In addition, it should be recognized that the size of the conductive cells 308 and the size of a spot of light can determine the minimum size of a droplet that can be manipulated by a microfluidic circuit. In one example, a conductive cell is about 50 μm by 100 μm, and about 20,000 conductive cells are deployed in an area of one square centimeter.

Figure 4A:
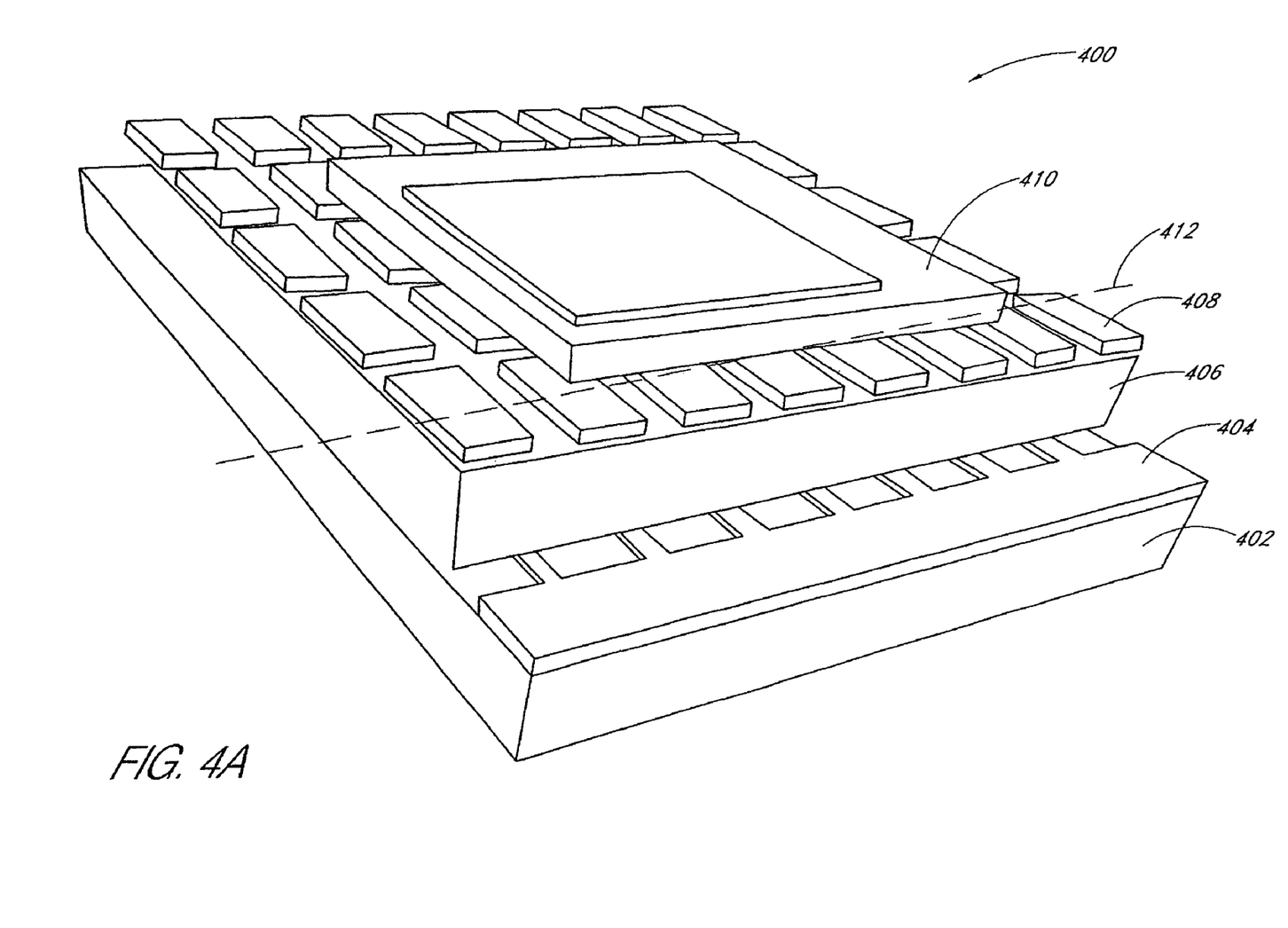
FIG. 4A is a perspective cutaway view of another embodiment of a substrate assembly that can provide an optical electro-wetting surface.

FIG. 4A is a perspective cutaway view of another embodiment of a substrate assembly 400 that can provide an optical electro-wetting surface. The perspective view of the substrate assembly 400 in FIG. 4A is illustrated in a cutaway and exploded manner. The illustrated substrate assembly 400 includes a base layer 402, an electrode layer 404, a layer of photoconductive material 406, a plurality of conductive cells 408, and an insulating layer 410.

The substrate assembly 400 illustrated in FIG. 4 advantageously provides a relatively low parasitic capacitance between the electrode layer 404 and the conductive cells 408. In addition, the configuration of the substrate assembly 400 shown in FIG. 4 provides relatively high resistance to dielectric breakdown for the layer of photoconductive material 406 between the electrode layer 404 and the conductive cells. The dielectric breakdown voltage can be relatively low, as the layer of photoconductive material 406 can be relatively thin. For example, the thickness of the layer of photoconductive material 406 is preferably between about 10 nm to about 1 micrometer. In one embodiment, the thickness of the layer of photoconductive material 406 is about 500 nanometers (nm). The higher dielectric breakdown voltage permitted by the substrate assembly 400 permits the biasing potential applied to a microfluidic circuit to be increased, thereby advantageously increasing the contact angle generated by the optical electro-wetting surfaces.

Figure 4B:
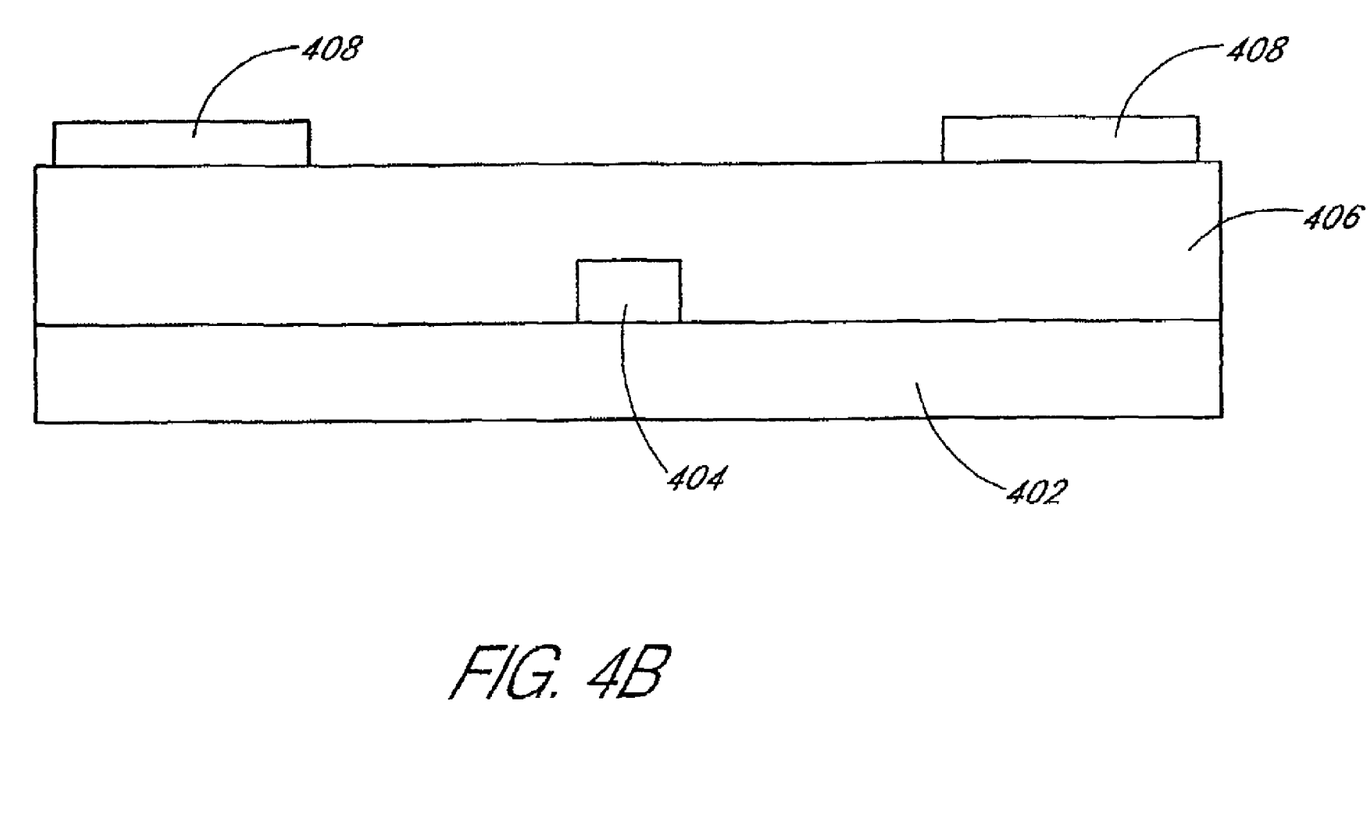
FIG. 4B is a cross-sectional view of a portion of the substrate assembly of FIG. 4A.

A cross-sectional view of a portion of the substrate assembly 400 taken along dashed line 412 is shown in FIG. 4B. As illustrated in FIG. 4B, the conductive cells 408 are laterally offset from corresponding lines of the electrode layer 404, thereby increasing the spacing between the conductive cells 408 and the lines of the electrode layer 404. Preferably, lines of the electrode layer 404 are relatively evenly spaced (laterally) between rows or columns of conductive cells 408. The lateral spacing between the lines of the electrode layer 404 and the conductive cells 408 are preferably relatively large compared to the thickness of the layer of photoconductive material 406. In one example, the lateral separation between a line of the electrode layer 404 and a conductive cell 408 is about 5 μm. In addition, the conductive cells 408 of the substrate assembly 400 illustrated in FIG. 4 can be formed from relatively easily fabricated shapes, such as squares, rectangles, circles, ellipses, and the like, and yet exhibit relatively low parasitic capacitance with the electrode layer 404.

Figure 5:
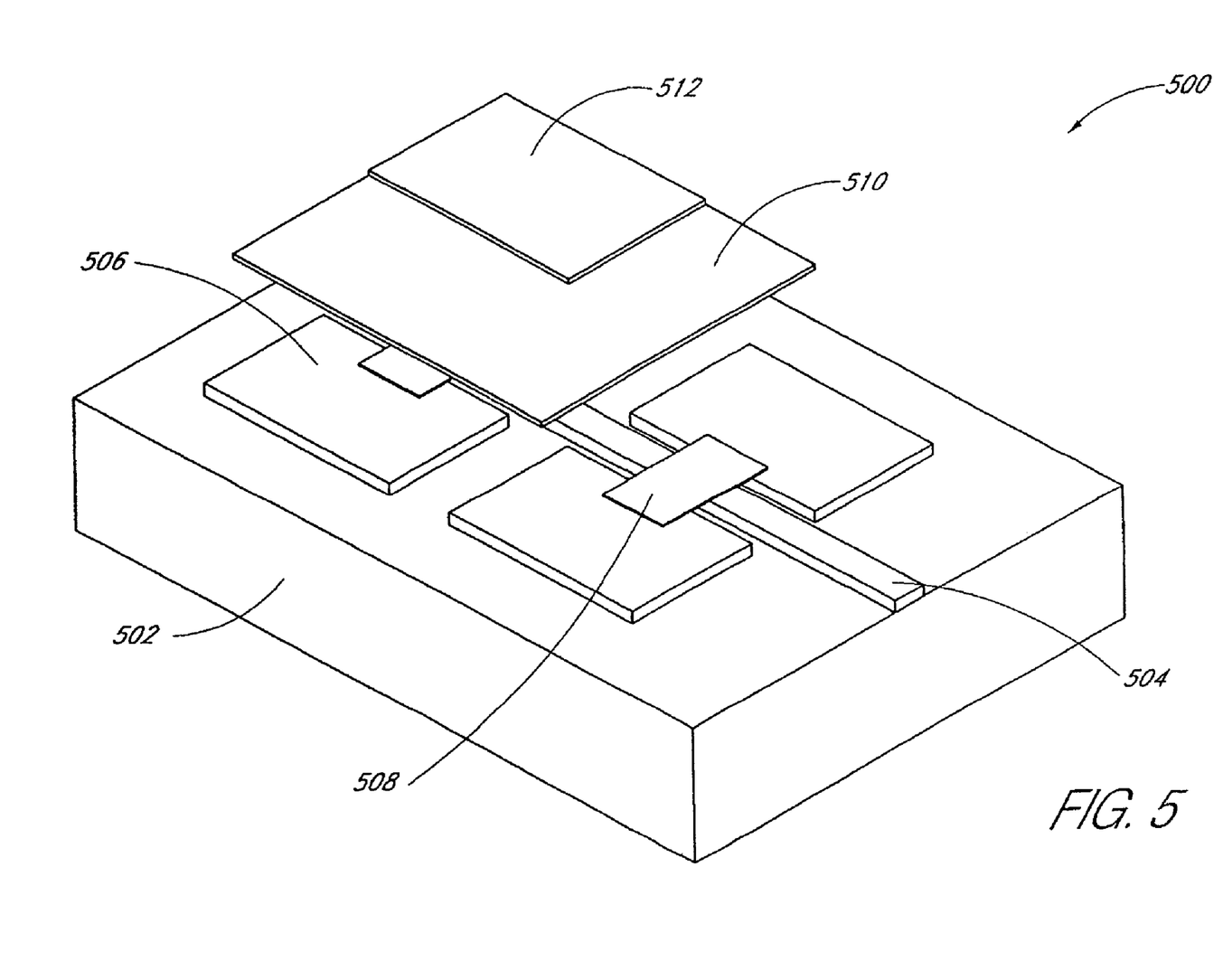
FIG. 5 is a perspective cutaway view of another embodiment of a substrate assembly that can provide an optical electro-wetting surface.

FIG. 5 is a perspective cutaway view of another embodiment of a substrate assembly 500 that can provide an optical electro-wetting surface. Advantageously, the substrate assembly 500 is relatively transparent, thereby facilitating the fabrication of a microfluidic circuit with two active optical electro-wetting surfaces. In addition, the illustrated substrate assembly 500 can be fabricated from a single layer of a conductor, thereby reducing fabrication steps and lowering manufacturing cost over embodiment with multiple conductor layers.

The substrate assembly 500 illustrated in FIG. 5 includes a base layer 502, an electrode 504, a plurality of conductive cells 506, a plurality of photoconductive cells 508, and an insulation layer. The illustrated insulation layer includes a multi-layer stack of a first layer 510 of an insulating material and a second layer 512. For example, the first layer 510 can be formed from a relatively thick layer of silicon oxide and the second layer 512 can be formed from a hydrophobic material such as PTFE. It will be understood that the size of the substrate assembly 500 can vary in a very broad range and that only a relatively small portion of the substrate assembly 500 is shown in FIG. 5.

The base layer 502 can be fabricated from an insulating material. The electrode 504, which is part of a plurality of electrodes, is coupled to a voltage reference, such as to a terminal of an AC voltage supply or to a ground reference. Notwithstanding conductive paths through the photoconductive cells 508, the conductive cells 506 are electrically isolated from each other and from the electrode 504. In one embodiment, the conductive cells 506 and the electrode 504 are formed and patterned from the same layer of material, such as from the same layer of indium tin oxide (ITO).

The photoconductive cells 508 are arranged to couple at least one conductive cell 506 to a corresponding electrode 504. In the illustrated embodiment of the substrate assembly 500, the photoconductive cell 508 couples a pair of conductive cells 506 to the electrode 504. Without illumination by light (other than ambient light), the photoconductive cells 508 have relatively low conductivity, and the corresponding conductive cells 506 are electrically floating. In response to illumination by light, the photoconductive cells 508 exhibit relatively high conductivity and ties the corresponding conductive cells 506 to the potential of the electrode 504. Although the illustrated photoconductive cells 508 are disposed between first layer 510 and the electrode 504 and/or the conductive cells 506, it will be understood that the photoconductive cells 508 can alternatively be disposed between the base layer 502 and the electrode 504 and/or the conductive cells 506.

In regions of the substrate assembly 500 where the conductive cells 506 are floating, there is relatively little potential difference applied to the portions of the first layer 510 and the second layer 512 disposed above the floating conductive cells 506. As a result, relatively little electric field exists at the surface of the substrate assembly 500 and a droplet has a relatively high contact angle at the corresponding surface. Where the conductive cells 506 are tied to the electrode 504, the corresponding portion of the first layer 510 and the second layer 512 is subjected to a relatively large voltage drop and a relatively strong electric field results at the surface of the second layer 512. The relatively strong electric field reduces the contact angle of the droplet at the surface, which permits the droplet to be manipulated by capillary action.

The substrate assembly 500 can be used both in microfluidic circuits with a single optical electro-wetting surface and in microfluidic circuits with two optical electro-wetting surfaces. Where it is desirable for the substrate assembly 500 to be relatively transparent, e.g., at least one wall or structure of a microfluidic circuit with two optical electro-wetting surfaces, the base layer 502 can be formed from a transparent material such as glass, and the electrode 504 and the conductive cells 506 can be formed from a relatively transparent conductor such as indium tin oxide (ITO).

Figure 6:
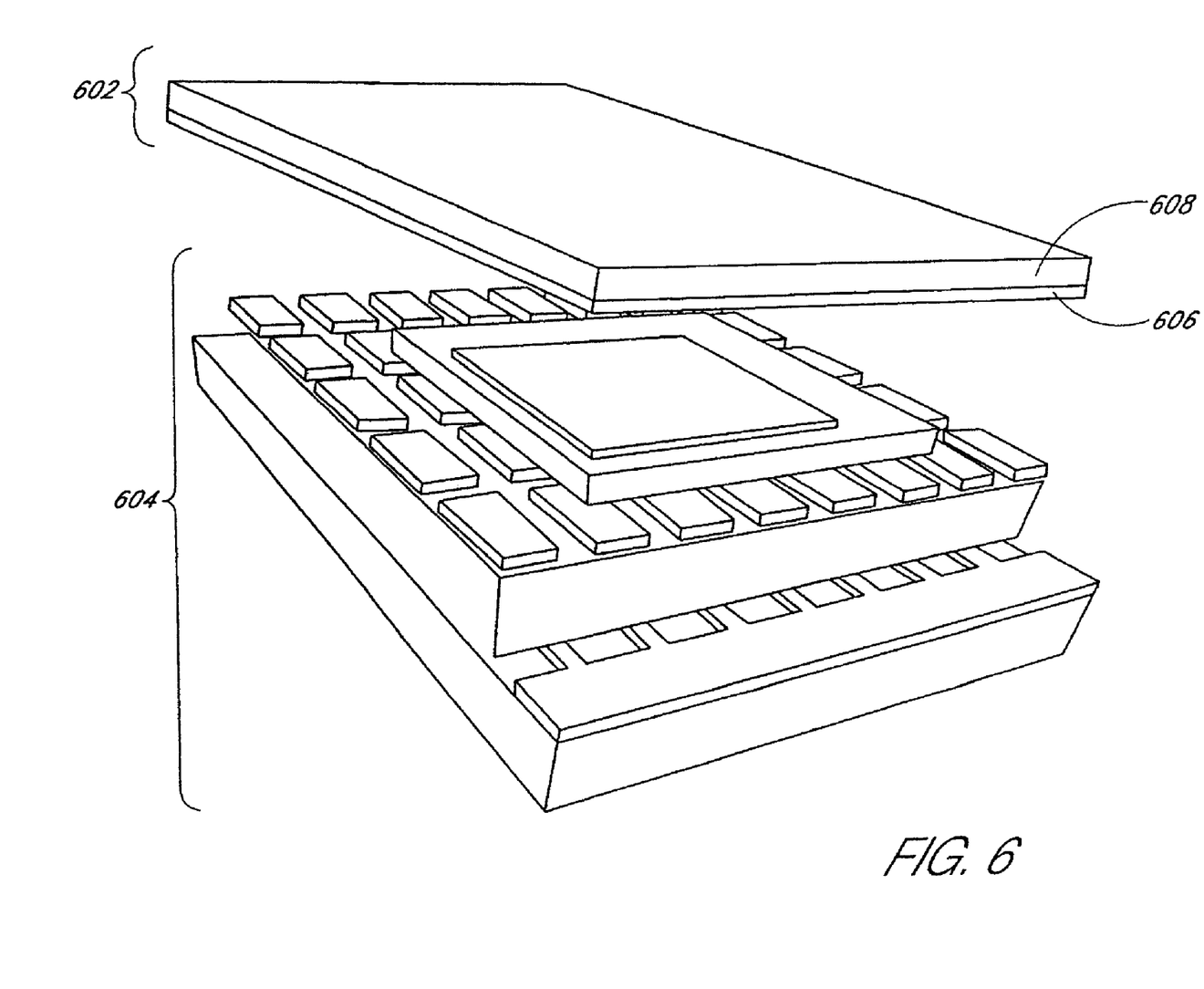
FIG. 6 is a perspective, exploded and cutaway view of a microfluidic circuit with one optical electro-wetting surface.

FIG. 6 is a perspective, exploded, and cutaway view of a microfluidic circuit 600 with one optical electro-wetting surface. The microfluidic circuit 600 includes a first structure 602 with a hydrophobic surface and a second structure 604 with an optical electro-wetting surface. A droplet is manipulated in a region between the first structure 602 and the second structure 604.

The illustrated first structure 602 includes a first layer 606 of an insulating material and a second layer 608 of a conductive material. The second layer 608 is coupled to a voltage reference, such as to a terminal of an AC voltage source. It will be understood by one of ordinary skill in the art that other layers, such as encapsulation layers, can also be included. Exemplary materials for the first layer 606 and for the second layer 608 include PTFE and indium-tin-oxide (ITO), respectively. The first layer 606 is preferably relatively thin, e.g., 20 nm, so that a relatively small amount of the voltage applied between the first structure 602 and the second structure 604 drops across the first layer 606.

The second structure 604 forms an optical electro-wetting surface in response to the applied voltage and light. For illustrative purposes, the second structure 604 illustrated in FIG. 6 corresponds to the substrate assembly 400 of FIG. 4A. However, the second structure 604 can also correspond to other structures that form optical electro-wetting surfaces, such as the structures described in connection with FIG. 3A and with FIG. 5.

As described earlier in connection with FIG. 2, a microfluidic circuit can be fabricated with two optical electro-wetting surfaces. Where two optical electro-wetting surfaces are used to manipulate a droplet, a single light beam from a single side of the microfluidic circuit can be used provided that at least one of the structures providing the optical electro-wetting surfaces is sufficiently transparent to allow light to pass through to the opposing structure. One embodiment of a sufficiently transparent substrate assembly has been described earlier in connection with FIG. 5. Advantageously, the optical electro-wetting surfaces can be activated by a beam of light, and complex alignment techniques that align control electrodes are not needed.

Figure 7:
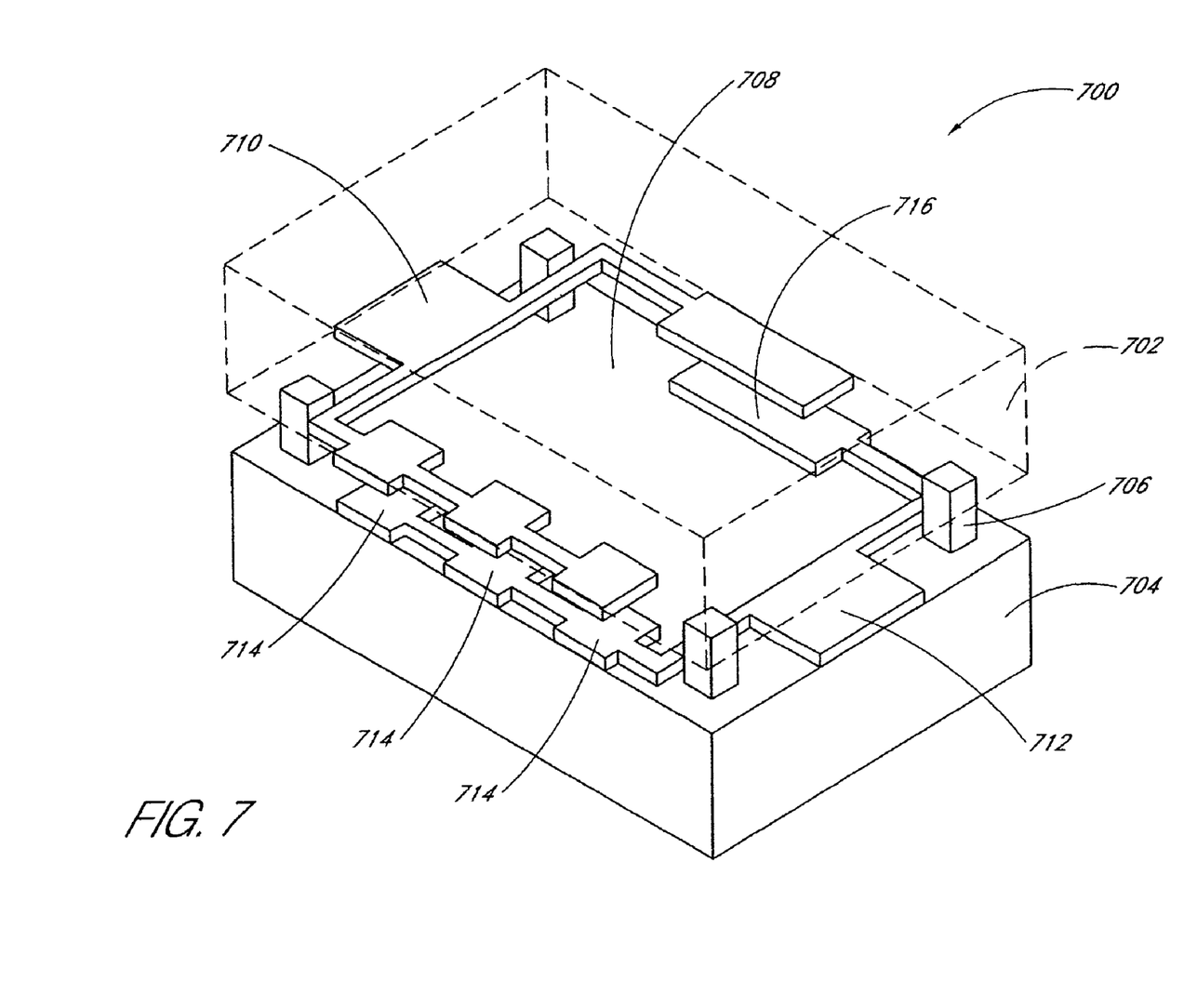
FIG. 7 illustrates one example of a lab-on-a-chip implemented with at least one optical electro-wetting surface.

FIG. 7 illustrates one example of a lab-on-a-chip 700 implemented with an optical electro-wetting surface. Preferably, the lab-on-a-chip 700 uses optical electro-wetting surfaces on inner surfaces of both an upper wall 702 and a lower wall 704. In one embodiment, the upper wall 702 and the lower wall 704 correspond to the substrate assembly 500 described earlier in connection with FIG. 5. In one embodiment, components of the upper wall 702 and the lower wall 704 can be symmetrically arranged such that identical walls can be used for the upper wall 702 and the lower wall 704.

A plurality of spacers 706 maintain spacing between the upper wall 702 and the lower wall 704, thereby providing a cavity in which to manipulate droplets. The spacers 706 can advantageously be formed from SU8, which is a photosensitive polymer that is readily patterned with photolithography techniques. It will be understood by one of ordinary skill in the art that the spacers 706 can be formed from a variety of materials. In one example, the spacers 706 maintain the gap between the upper wall 702 and the lower wall 704 to a range between about 50 micrometers (µm) and about 100 µm. However, it will be understood that the gap between the upper wall 702 and the lower wall 704 can correspond to an even broader range.

Droplets are transported to a liquid operation area 708, which can be located approximately in the center of the lab-on-a-chip 700. Various operations, such as transporting, merging, mixing, cutting, and the like, can be performed in the liquid operation area 708. As described earlier in connection with FIGS. 1 and 2, the upper wall 702 and the lower wall 704 are coupled to a voltage bias, such as an AC voltage source. In addition, the upper wall 702 includes an upper electrode 710, and the lower wall 704 includes a lower electrode 712. The upper electrode 710 and the lower electrode 712 are also biased, and are preferably biased by the same voltage bias as the upper wall 702 and the lower wall 704, respectively.

The upper electrode 710, as well as the lower electrode 712, can be fabricated in a separate layer or can be fabricated in the same layer as existing electrodes. In one embodiment, the upper wall 702 corresponds to the substrate assembly 500 of FIG. 5, the upper electrode 710, and the electrode 504, and the conductive cells 506 are formed from the same layer of conductive material. The upper electrode 710 is preferably coupled to the voltage bias corresponding to the electrode 504 without coupling from photoconductive cells 508. This permits electrical biasing to be provided to regions corresponding to the upper electrode 710 and the lower electrode 712 when the lab-on-a-chip 700 is in a powered-on state.

The electrical biasing between the upper electrode 710 and the lower electrode 712 advantageously attracts droplets for storage and disposal. For example, a plurality of reservoirs 714 maintain chemicals that can be introduced to the liquid operation area 708. A waste region 716 corresponds to a reservoir that stores waste chemicals, such as excess droplets.

FIGS. 8A-D illustrate examples of manipulation or actuation of droplets with an optical electro-wetting surface. In FIGS. 8A-D, the square areas correspond to conductive cells. These conductive cells are floating when not illuminated and are tied to a bias reference (which can include ground) when illuminated by a light source, such as a laser. It will be understood that a single laser can be pulsed to create multiple spots of light. Also, mirrors can be used to direct the laser light. In addition, LED arrays can also advantageously provide relatively precise control of light. Moreover, although an LED array can correspond to a relatively large number of LEDs to control, LEDs can be switched on and off with direct current (DC) voltage at a relatively low voltage level, which is much more easily switched than relatively high voltage AC voltage Also, the LED array can be separate, rather than integral with the optical electro-wetting surface, so that the LED array does not have to be disposed with the disposal of microfluidic circuit fabricated with an optical electro-wetting surface. Further advantageously, the optical electro-wetting surfaces can be activated by a single light source of a single wavelength that is within the visible light spectrum.

Figure 8A:
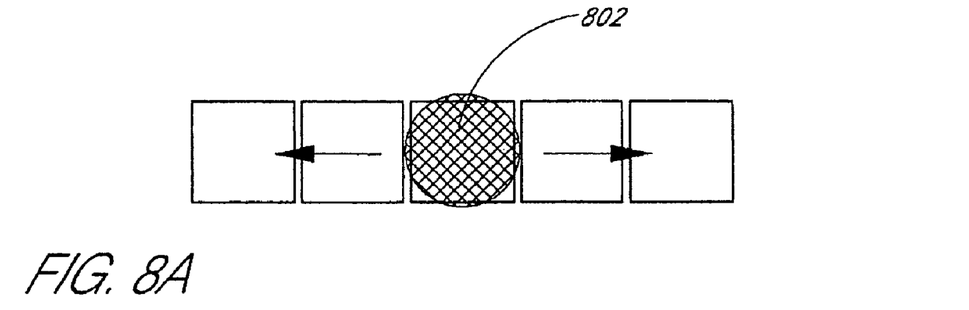
FIGS. 8A-D illustrate examples of manipulation or actuation of droplets with an optical electro-wetting surface.

FIG. 8A illustrates transporting a droplet 802. To transport the droplet 802, a spot of light sequentially activates adjacent areas of the conductive cells to drive the droplet 802.

Figure 8B:
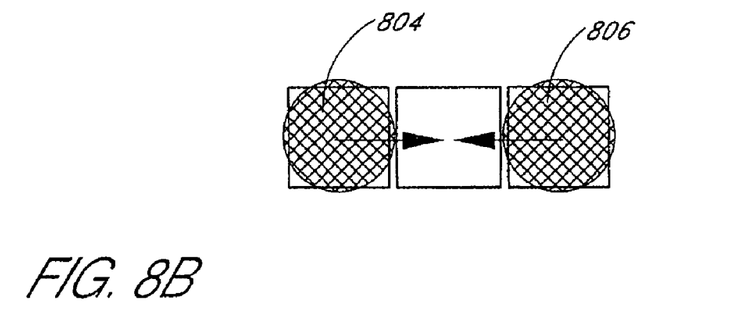

FIG. 8B illustrates joining a first droplet 804 and a second droplet 806 together to create a larger droplet. It will be understood that more than two droplets can also be joined. Joining droplets can advantageously be used to mix chemicals together. To join droplets, a spot of light can transport one droplet to another or spots of light can be used to simultaneously transport at least two droplets to each other.

Figure 8C:
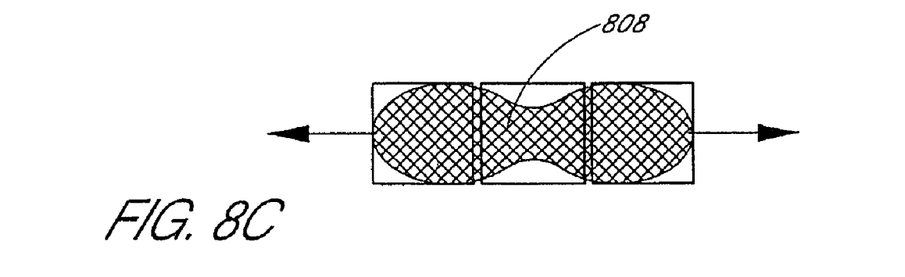

FIG. 8C illustrates cutting or separating a droplet 806 into at least two droplets. To cut, at least two spots of light gradually separate, thereby leaving at least two droplets.

Figure 8D:
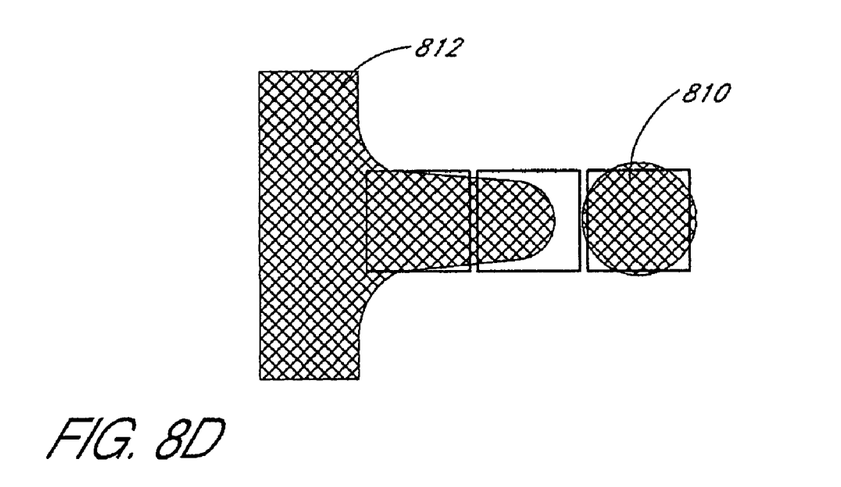

FIG. 8D illustrates creating a droplet 810 from a reservoir of fluid 812, such as the reservoir 714 described earlier in connection with FIG. 7. The droplet 810 can be created by using a light spot to pull and gradually separate a droplet from the reservoir of fluid 812. In one embodiment, the corresponding reservoir 714 need not be illuminated by a light source because the reservoir is already biased as described earlier in connection with FIG. 7.

Various embodiments of the invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of manipulating a droplet, comprising:
    providing a first plate and a second plate electrically coupled to a bias voltage;
    said first and second plates having opposing surfaces;
    placing at least one droplet between the opposing surfaces of the first and second plates; and
    selectively illuminating portions of at least one opposing surface of the first plate or the second plate such that the illuminated portion induces a gradient in surface tension of the droplet;
    wherein the gradient in the surface tension imparts motion to the droplet, thereby facilitating manipulation of the droplet.

2. A method as recited in claim 1, wherein said manipulation is selected from the group consisting essentially of dividing said droplet, joining said droplet with one or more other droplets, creating a droplet from a reservoir of liquid and moving said droplet from a first position to a second position.

3. A method as recited in claim 1, wherein said droplet is placed between opposing surfaces of said first and second plates, said surface of said first plate further comprising a hydrophobic surface.

4. A method as recited in claim 1:
    wherein a cavity is formed with a plurality of spacers interposed between said first and second plates; and
    wherein said droplet is positioned in said cavity for manipulation.

5. A method as recited in claim 1, wherein at least one of said opposing surfaces comprises a photoconductive layer.

6. A method as recited in claim 5:
    wherein said bias voltage comprises an alternating current (AC) voltage bias electrically coupled to the first plate and to the second plate, wherein the AC voltage bias generates an electric field between the first plate and the second plate; and
    wherein said gradient in surface tension of said droplet is induced by illumination of at least a portion of said photoconductive layer.

7. A method as recited in claim 6, wherein the illuminated portion of the photoconductive layer exhibits lower electrical resistivity than non-illuminated portions thereby inducing a gradient in the electric field in a corresponding area adjacent to the photoconductive layer.

8. A method of manipulating a droplet, comprising:
    providing a first plate and a second plate;
    said first and second plates having opposing surfaces;
    said first and second plates coupled to a voltage bias source;
    wherein at least one of said opposing surfaces comprises a photoconductive layer;
    placing a droplet between the opposing surfaces of the first and second plates; and
    selectively illuminating portions of said photoconductive layer such that the illuminated portion induces a gradient in surface tension of the droplet;
    wherein the gradient in the surface tension imparts motion to the droplet, thereby facilitating manipulation of the droplet.

9. A method as recited in claim 8, wherein said manipulation is selected from the group consisting essentially of dividing said droplet, joining said droplet with one or more other droplets, creating a droplet from a reservoir of liquid and moving said droplet from a first position to a second position.

10. A method as recited in claim 8, further comprising:
    providing a plurality of spacers between said first and second plates thereby forming a cavity between said first and second plates;
    wherein said droplet is positioned in said cavity for manipulation.

11. A method as recited in claim 8, wherein the illuminated portion of the photoconductive layer exhibits lower electrical resistivity than non-illuminated portions thereby inducing a gradient in the electric field in a corresponding area adjacent to the photoconductive layer.

12. A method of manipulating a droplet, comprising:
    providing a first plate and a second plate electrically coupled to a bias voltage;
    said first and second plates having opposing surfaces;
    providing a source of light configured to impinge upon portions of said opposing surfaces of said first and second plates in a predetermined locations and sequence over time;
    placing a plurality of droplets between the opposing surfaces of the first and second plates; and
    selectively illuminating portions of at least one opposing surface of the first plate or the second plate according to the sequence such that the illuminated portion induces a gradient in surface tension of the droplets;
    wherein the gradient in the surface tension imparts motion to the droplets, thereby facilitating manipulation of the droplets.

13. A method as recited in claim 12, wherein at least one of said opposing surfaces of said first and second plates comprises a photoconductive layer.

14. A method as recited in claim 12, wherein at least one of said opposing surfaces of said first and second plates has a hydrophobic layer.

15. A method as recited in claim 12, wherein said first plate is transparent and said opposing surface of said second plate comprises a photoconductive layer.

16. A method as recited in claim 12, wherein said first and second plates are illuminated by pulses of laser light.

17. A method as recited in claim 12, wherein said first and second plates are illuminated by a LED array.

18. A method as recited in claim 15, wherein said photoconductive layer of said second plate is illuminated by spots of light transmitted through said first plate.

19. A method as recited in claim 12:

wherein said bias voltage comprises an alternating current (AC) voltage bias electrically coupled to the first plate and to the second plate, wherein the AC voltage bias generates an electric field between the first plate and the second plate; and wherein said gradient in surface tension of said droplet is induced by illumination of at least a portion of said photoconductive layer.

* * * * *